United States Patent [19]

De Jong et al.

[11] Patent Number: 5,302,903
[45] Date of Patent: Apr. 12, 1994

[54] MASTITIS DETECTOR FOR DAIRY CATTLE

[75] Inventors: Hendrik J. De Jong, Groenlo; Albertino B. M. Verstege, Aalten; Pieter H. Hogewerf, Wageningen, all of Netherlands

[73] Assignee: N.V. Nederlandsche Apparatenfabriek NEDAP, De Groenlo, Netherlands

[21] Appl. No.: 959,536

[22] Filed: Oct. 13, 1992

Related U.S. Application Data

[63] Continuation of Ser. No. 520,199, May 9, 1990, abandoned.

[30] Foreign Application Priority Data

May 10, 1989 [NL] Netherlands ............... 8901165

[51] Int. Cl.$^5$ ............................................. G01N 27/02
[52] U.S. Cl. .................................. 324/446; 324/450
[58] Field of Search .............. 324/438, 439, 441, 446, 324/449, 450, 696, 724, 425; 19/14.14

[56] References Cited

U.S. PATENT DOCUMENTS

| | | | |
|---|---|---|---|
| 2,000,668 | 5/1935 | Pease | 324/446 X |
| 2,505,936 | 5/1950 | Behn | 324/441 |
| 2,836,792 | 5/1958 | Weber | 324/450 |
| 3,884,187 | 5/1975 | Massie et al. | 119/14.14 |
| 3,989,009 | 11/1976 | Robar et al. | |
| 4,227,151 | 10/1980 | Ellis et al. | 324/441 X |
| 4,325,028 | 4/1982 | Takahashi | 324/442 |
| 4,638,291 | 1/1987 | Puscasu | 324/696 X |

FOREIGN PATENT DOCUMENTS

| | | | |
|---|---|---|---|
| B12229177 | 8/1978 | Australia . | |
| 3308361 | 9/1984 | Fed. Rep. of Germany . | |
| 2303286 | 10/1976 | France . | |
| 6915152 | 4/1971 | Netherlands . | |
| 8301231 | 11/1984 | Netherlands . | |
| 1438282 | 6/1976 | United Kingdom | 324/450 |

*Primary Examiner*—Kenneth A. Wieder
*Assistant Examiner*—Maura K. Regan
*Attorney, Agent, or Firm*—Jacobson, Price, Holman & Stern

[57] ABSTRACT

A throughflow type mastitis detector having an inlet stub and an outlet stub by means of which the mastitis detector can be coupled to a milk tube; a measuring chamber having side walls, a closed bottom, and an opening opposite said bottom in spaced relationship to said inlet stub, through which opening the milk to be monitored, supplied through the inlet stub, can flow into the measuring chamber, and through which the milk can again leave the measuring chamber when the level of the milk within the measuring chamber exceeds the height of the lowest side wall portion; and a pair of electrodes in the bottom of said measuring chamber for measuring the electrical conductivity of the milk, characterized in that at least one of the electrodes has a convex head projecting above the bottom surface and a shank extending through an opening in the bottom.

10 Claims, 2 Drawing Sheets

MASTITIS DETECTOR FOR DAIRY CATTLE

This is a continuation of application Ser. No. 07/520,199, filed May 9, 1990 which was abandoned upon the filing hereof.

This invention relates to a mastitis detector of the throughflow type, comprising an inlet stub and an outlet stub by means of which the mastitis detector can be coupled with a milk tube; a measuring chamber having side walls, a closed bottom, and an opening opposite said bottom in spaced relationship to said inlet stub, through which opening the milk to be monitored, supplied through the inlet stub, can flow into the measuring chamber, and through which the milk can again leave the measuring chamber when the level of the milk within the measuring chamber exceeds the height of the lowest side wall portion; and a pair of electrodes in the bottom of said measuring chamber for measuring the electrical conductivity of the milk.

A similar detector is disclosed in German Offenlegungsschrift 3,308,361. One advantage of the throughflow type of mastitis detector is that such a detector can be permanently mounted in the milk tube of a milking machine, so that the milk can be checked automatically and directly each time a cow is milked, without it being necessary for separate samples to be taken, which should then be examined later and often elsewhere. In addition, a throughflow detector lends itself particularly well for being permanently mounted in the short milk tubes, i.e., in the milk tubes between the milk claw and the teat cups. If a throughflow type of mastitis detector is provided in each of the short milk tubes, an incipient mastitis can be most rapidly detected, and in addition it can be directly detected in which part of the udder the inflammation occurs. This also creates the possibility for the milk from the affected part of the udder to be discharged to a separate container through a controllable valve in the short milk tube and/or the milk claw, provided for the purpose. The milk from the other parts of the udder, which at that moment is still excellently fit for human consumption, can be collected and processed further in the usual way.

It is known that both clinical and subclinical mastitis infections in milk cattle can be diagnosed, among other means, on the ground of the altered pattern in the electrical conductivity of the milk which, in the case of a mastitis infection is substantially increased in a characteristic way. During the milking process of, for example, a cow, the variation of the conductivity of the milk is recorded per quarter—i.e., the part of a cow's udder drained by one teat. From the history of the conductivity, it can be derived whether it is substantially increased at a particular moment. The electrical conductivity can be measured, for example, by means of electrodes between which an A.C. voltage prevails. Such a method is known from Netherlands patent application No. 83,01231.

One disadvantage of the mastitis detector disclosed in German Offenlegungsschrift 3,308,361 is that it has electrodes which are electrically spaced very closely together. Consequently, when this detector is used for measuring the conductivity of the milk in the measuring chamber, only a short measuring path through the milk is available. As a consequence, spurious factors, such as the transition resistance between the electrodes and the milk have a relatively great influence on the result of the measurement. Indeed, the accuracy of a conductivity measurement of the milk in the measuring chamber using the known throughflow meter leaves something to be desired. By way of an alternative, the known detector could be equipped with a much wider measuring chamber, but this gives the detector a bulky size, which is undesirable.

Another disadvantage of the known throughflow detector is that a gap can be formed along the circumference of the electrodes, as a result of the electrodes and the plastic material of the bottom having different coefficients of thermal expansion. Such gaps are difficult to clean, and there is the danger that a bacterial colony develops in such gaps.

It is an object of the present invention to overcome the disadvantages outlined above and, quite generally, to provide a reliable mastitis detector of the throughflow type.

For this purpose, the present invention provides a mastitis detector as defined in the opening paragraph of this specification, which is characterized in that at least one of the electrodes has a convex head projecting above the bottom surface and a shank extending through an opening in the bottom.

One embodiment of the invention will now be described, by way of example, with reference to the accompanying diagrammatic drawings. In said drawings, FIG. 1 shows a longitudinal sectional view of one embodiment of a mastitis detector according to the present invention;

Figure 1:
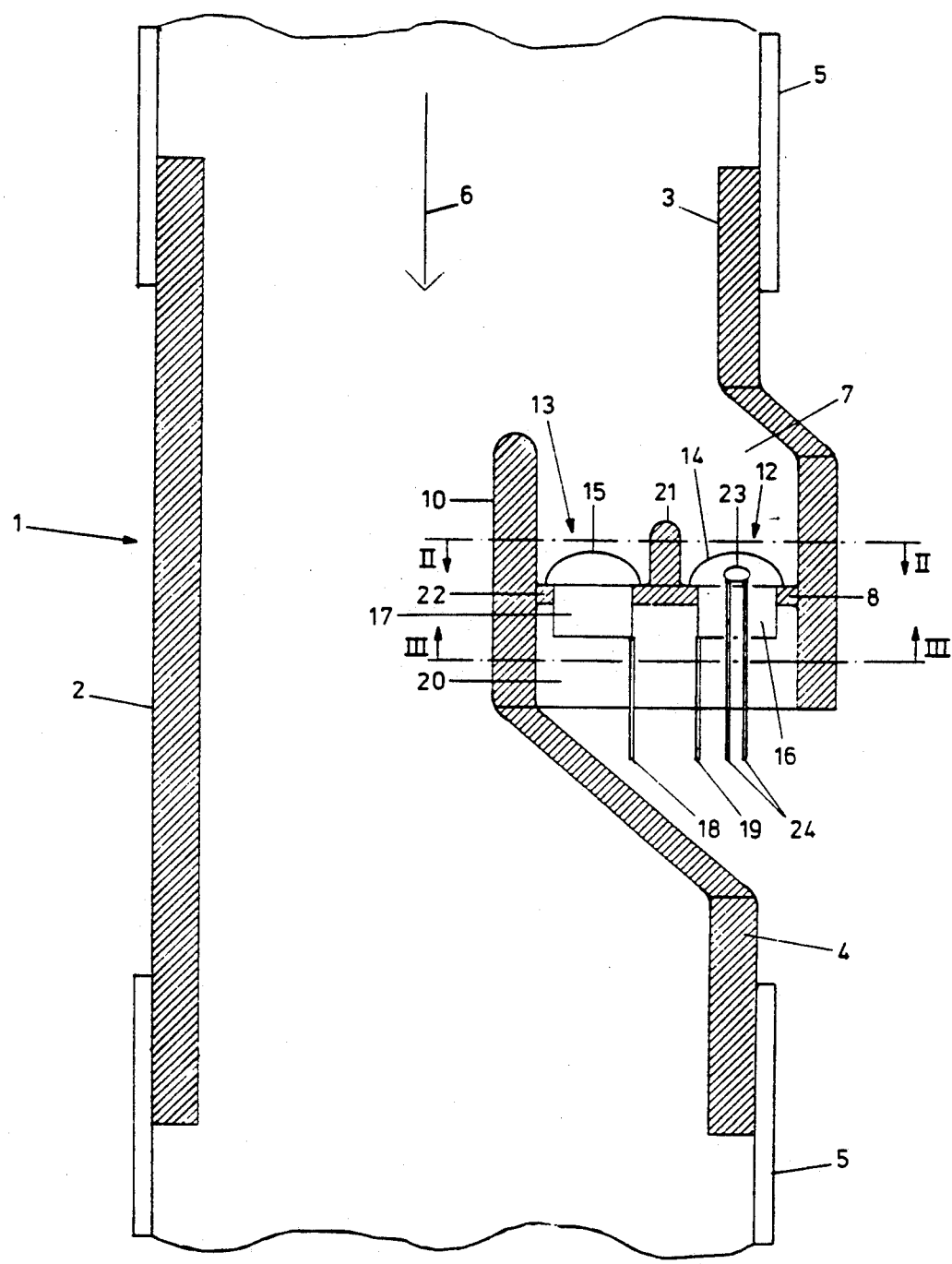
Figure 2:
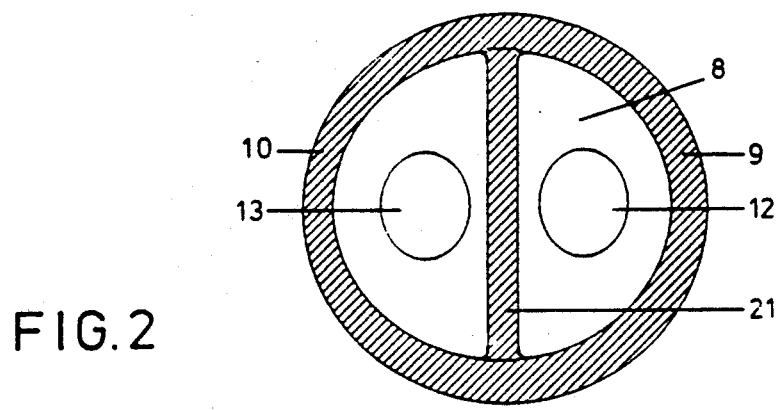
FIG. 2 shows a cross-sectional view, taken on the line II—II of FIG. 1.
Figure 3:
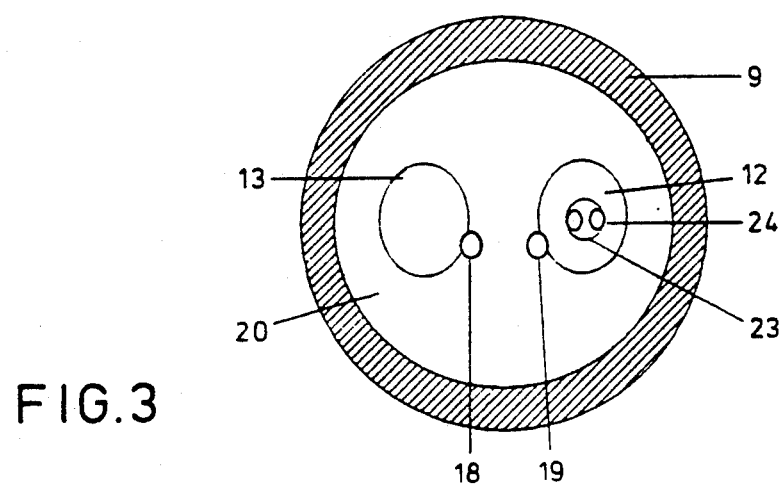
FIG. 3 shows a cross sectional view, taken on the line III—III of FIG. 1.

FIG. 1 shows diagrammatically and in longitudinal sectional view an example of a mastitis detector 1 according to the present invention. The detector comprises a housing or body 2 with an inlet stub 3 and an outlet stub 4, with which the body can be mounted in a milk tube 5. The direction of the milk stream is indicated by an arrow 6. The housing or body is made of an electrically insulating material, for example, a suitable synthetic plastics.

Formed in body 1 is a measuring chamber 7, which is laterally off-set relative to the longitudinal axis of the inlet stub. The measuring chamber has a closed bottom 8, and side walls 9 and 10, partly merging with the wall of the inlet stub and partly with the wall of the outlet stub. The side walls are formed so as to provide a lowered portion 11 through which milk collected by the measuring chamber may flow out of the chamber. A minimum level of milk is maintained in the measuring chamber, defined by the height of the lowered portion relative to bottom 8.

The measuring chamber forms, as it were, a cup provided against the inner wall of body 2, whose opening faces the inlet stub.

Provided in the bottom of the measuring chamber are two electrodes 12, 13. The electrodes are each approximately mushroom shaped with a convex head 14, 15, projecting above the surface of bottom 8 of the measuring chamber, and a shank 16, 17 extending through an opening in the bottom. The electrodes are preferably made of stainless steel and are preferably hollow with thin walls. Furthermore, the electrodes are preferably finished smooth on the outside, so as to prevent fouling. Owing to the convex shape, a relatively large contacting surface is presented to the milk supplied to the measuring chamber, which, like the smooth finish, promotes effective electrical contact with the milk.

The electrodes are provided with connecting wires 18, 19, which in the example shown are attached to the shanks 16, 17. The shanks extend through bottom 8 into a mass 20 of electrically and thermally insulating material, for example, epoxy resin.

Provided in the measuring chamber between electrodes 12, 13 is a partition 21, serving to lengthen the measuring path between the electrodes. The effect of any transition resistance between the electrodes and the milk during the measurement of the conductivity of the milk is thus still further reduced.

By virtue of the use of the convex electrodes and the partition, the measuring chamber may be relatively small, and accordingly, the entire mastitis detector may be of small design. A mastitis detector according to the present invention is thus highly suitable for being permanently mounted in the milk tubes.

In the embodiment shown, the shank of an electrode has a smaller diameter than the convex part. This provides a shoulder 22, by which the convex part rests on the bottom 8 of the measuring chamber, and with a suitable construction of the shank can be pulled with some force into contact with the bottom 8. If desired, the shoulder may be somewhat undercut. Any gap which may be formed during use between the shank and the bore in the bottom in which the shank is placed will then remain inaccessible to the milk in the measuring chamber, so that no fouling can take place in such a gap.

Furthermore, in the embodiment shown, a temperature sensor 23 is provided in one of the electrodes, which can be done without any problems owing to the convex and hollow shape of the electrodes. The temperature sensor has connecting wires 24 and may be a temperature-sensitive resistor, such as an MTC resistor. The temperature sensor is preferably brought into proper thermal contact with the electrode concerned by means of known per se heat-conductive paste. The convex electrode shape and the thin wall of the electrodes promote a good thermal contact with the milk, so that an accurate measurement of the temperature is possible. As mastitis leads to an increase in temperature of the milk, a highly reliable mastitis detection can be realized by comparing the result of the conductivity measurement with the result of the temperature measurement.

The design of the mastitis detector shown is such that it can be cleaned in a simple manner. By reversing the detector or the tube or milk claw mounting the detector, all residual milk or cleaning fluid will flow out of the detector.

The operation of the mastitis detector is as follows. When the mastitis detector is placed in the milking system, it should be so positioned that the milk flows over the electrodes in the measuring chamber. Furthermore, it is of importance that the milk does not experience undue resistance from the mastitis detector and its housing. When the milk, or a representative part thereof, is supplied to the detector in a space specially provided for the purpose, formed by the housing, periodical measurements of the electrical conductivity and temperature of the milk start. The results of the measurements can be processed in a process computer which compares the results of the measurements with the history of the conductivity and the temperature of the milk and provides an attention signal when substantial differences are detected. Mastitis can be detected in a simple manner at any desired point in the milking system by means of the detector according to the present invention. It is recommendable, however, for the mastitis detector to be mounted in a milk claw or in a milk tube of a milking system, and this preferably one detector for the milk stream of each individual test. An important advantage of measuring per teat, and hence per (udder) quarter is that the alterations in conductivity can be measured more clearly than after the milk from the four quarters has been mixed. The fact is that mastitis virtually always arises in one of the quarters. Moreover, if desired, any contaminated milk can be separately discharged per quarter through an electrically operated valve.

It is observed that, after reading the foregoing, various modifications will readily occur to one skilled in the art. Thus, if desired, a temperature sensor may be placed in both electrodes. Also, the partition may be formed with a broadened upper edge to increase the measuring path still further. The electrodes may have a threaded shank, so, that they may be mounted by means of a nut screwed on the shank against the bottom surface of bottom 8. Also the electrodes may, for example, be provided with a solid thinner central shank.

Figure 4:
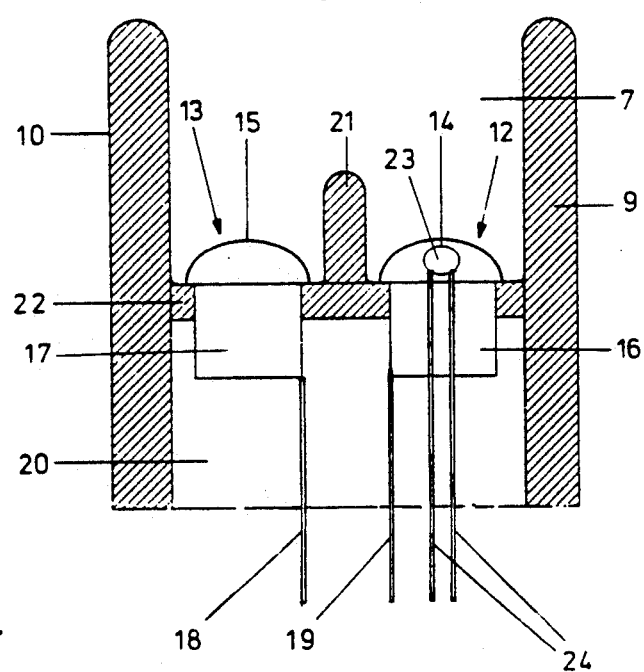
FIG. 4 shows a loose measuring chamber unit for a mastitis detector according to the present invention.

It is further observed that the measuring chamber, provided with electrodes and partition, as described above, may be made as a loose unit, and then mounted, for example, in the milk claw or any other part of a milking system. One embodiment of such a loose measuring chamber unit is shown diagrammatically in the accompanying FIG. 4.

The above and similar modifications are deemed to fail within the scope of the present invention.

We claim:

1. In a throughflow-type mastitis detector comprising an inlet stub and an outlet stub by means of which the mastitis detector is coupled to a milk tube; a measuring chamber having side walls, a closed bottom, and an opening opposite said bottom in spaced relationship to said inlet stub, through which opening the milk to be monitored, supplied through the inlet stub, flows into the measuring chamber, and through which the milk can again leave the measuring chamber when the level of the milk within the measuring chamber exceeds the height of the lowest side wall portion; and a pair of electrodes in the bottom of said measuring chamber for measuring the electrical conductivity of the milk, the improvement which comprises that at least one of the electrodes has a head projecting above the surface of the closed bottom and a shank extending through an opening in the bottom wherein said head has a larger diameter than the shank and presents a shoulder portion resting flush on the surface of said closed bottom such that no gaps exist substantially perpendicular with respect to the surface of the closed bottom between the closed bottom and the head of said at least one electrode, whereby bacteria colonies are prevented from developing between said at least one of the electrodes and the closed bottom of said measuring chamber.

2. A mastitis detector as claimed in claim 1, characterized in that at least the convex head is hollow.

3. A mastitis detector as claimed in claim 2, characterized in that the convex head has a thin wall.

4. A mastitis detector as claimed in claim 2, characterized by a temperature sensor provided in the hollow convex head of at least one of the electrodes.

5. A mastitis detector as claimed in claim 1, characterized by a partition formed on the bottom of the measuring chamber between the electrodes, said partition being lower than the lowest side wall portion.

6. A mastitis detector as claimed in claim 1, characterized in that at least the heads of the electrodes are finished smooth.

7. A mastitis detector as claimed in claim 1, wherein said shank is hollow.

8. A mastitis detector as claimed in claim 1, wherein said at least one of the electrodes is a hollow electrode having a thin electrode wall.

9. A measuring chamber unit for mastitis detection, comprising a measuring chamber with side walls, a closed bottom, and an open top, and two electrodes mounted in said bottom, characterized in that at least one of the electrodes has a head projecting above the surface of the closed bottom and a shank extending through an opening in the bottom wherein said head has a larger diameter than the shank and presents a shoulder portion resting flush on the surface of said closed bottom such that no gaps exist substantially perpendicular with respect to the surface of the closed bottom between the closed bottom and the head of said at least one electrode, whereby bacteria colonies are prevented from developing between said at least one of the electrodes and the closed bottom of said measuring chamber.

10. A unit as claimed in claim 9, characterized by a partition formed on the bottom of the measuring chamber between the electrodes.

* * * * *